(12) United States Patent
Zhang et al.

(10) Patent No.: US 10,869,963 B2
(45) Date of Patent: Dec. 22, 2020

(54) LOW-COST AMBULATORY MEDICAL PUMP

(71) Applicant: Zyno Medical, LLC, Natick, MA (US)

(72) Inventors: Mei Zhang, Sharon, MA (US); Chao Young Lee, Weston, MA (US)

(73) Assignee: Zyno Medical, LLC, Natick, MA (US)

( * ) Notice: Subject to any disclaimer, the term of this patent is extended or adjusted under 35 U.S.C. 154(b) by 0 days.

(21) Appl. No.: 16/207,620

(22) Filed: Dec. 3, 2018

(65) Prior Publication Data
US 2019/0099552 A1  Apr. 4, 2019

Related U.S. Application Data

(63) Continuation of application No. 14/471,102, filed on Aug. 28, 2014, now abandoned.

(51) Int. Cl.
| | | |
|---|---|---|
| *A61M 5/142* | (2006.01) | |
| *A61M 5/14* | (2006.01) | |
| *F04B 43/12* | (2006.01) | |
| *F04B 43/08* | (2006.01) | |
| *F04B 43/00* | (2006.01) | |
| *A61M 39/28* | (2006.01) | |

(52) U.S. Cl.
CPC ...... *A61M 5/14244* (2013.01); *A61M 5/1413* (2013.01); *A61M 5/14228* (2013.01); *F04B 43/0072* (2013.01); *F04B 43/082* (2013.01); *F04B 43/12* (2013.01); *A61M 39/284* (2013.01); *A61M 2005/14292* (2013.01); *A61M 2205/502* (2013.01); *A61M 2205/505* (2013.01); *A61M 2205/507* (2013.01); *A61M 2205/52* (2013.01)

(58) Field of Classification Search
CPC .......... A61M 5/14228; A61M 5/14232; A61M 39/284; F04B 45/08; F04B 45/06; F04B 45/065; F04B 43/12; F04B 43/08; F04B 43/082; F04B 43/207
See application file for complete search history.

(56) References Cited

U.S. PATENT DOCUMENTS

| | | | |
|---|---|---|---|
| 4,559,038 A | 12/1985 | Berg et al. | |
| 4,808,167 A | 2/1989 | Mann et al. | |
| 4,873,623 A | 10/1989 | Lane et al. | |
| 5,153,827 A | 10/1992 | Coutre et al. | |
| 5,165,874 A | 11/1992 | Sancoff et al. | |
| 5,239,319 A * | 8/1993 | Miyazaki | A61M 5/172 310/316.01 |
| 5,308,333 A | 5/1994 | Skakoon | |
| 5,322,422 A | 6/1994 | Natwick et al. | |
| 5,395,320 A * | 3/1995 | Padda | A61M 5/14228 128/DIG. 12 |

(Continued)

OTHER PUBLICATIONS

"Technical Manual CADD-Legacy Ambulatory Infusion Pumps", Smiths Industries Medical Systems, Jan. 2000.

(Continued)

*Primary Examiner* — Jenna Zhang
(74) *Attorney, Agent, or Firm* — Boyle Fredrickson S.C.

(57) ABSTRACT

A low-cost medical pump for ambulatory use provides reduced life components combined with a pump lockout enforcing a safe operating limit and preventing reuse after that limit is exceeded. An improved IV line clamp portion minimizes unsupported clamp structure length and provides a dual lock system preventing inadvertent clamp release.

18 Claims, 4 Drawing Sheets

(56) References Cited

U.S. PATENT DOCUMENTS

| | | | |
|---|---|---|---|
| 5,432,934 A | 7/1995 | Levin et al. | |
| 5,482,446 A * | 1/1996 | Williamson | A61M 5/142 |
| | | | 417/234 |
| 5,620,312 A | 4/1997 | Hyman et al. | |
| 5,681,285 A | 10/1997 | Ford et al. | |
| 5,695,473 A | 12/1997 | Olsen | |
| 5,788,671 A | 8/1998 | Johnson | |
| 5,843,035 A | 12/1998 | Bowman et al. | |
| 5,993,420 A * | 11/1999 | Hyman | A61M 5/142 |
| | | | 604/131 |
| 6,123,686 A | 9/2000 | Olsen et al. | |
| 6,172,479 B1 | 1/2001 | Barton | |
| 6,554,798 B1 | 4/2003 | Mann et al. | |
| 6,752,787 B1 | 6/2004 | Causey, III et al. | |
| 7,963,131 B2 * | 6/2011 | Zhang | E05B 73/0023 |
| | | | 70/57 |
| 8,552,880 B2 | 10/2013 | Kopp et al. | |
| 8,694,331 B2 | 4/2014 | Debelser et al. | |
| 8,768,717 B2 | 7/2014 | Blomquist | |
| 8,858,526 B2 | 10/2014 | Blomquist | |
| 8,882,701 B2 | 11/2014 | Debelser et al. | |
| 8,974,415 B2 | 3/2015 | Robert et al. | |
| 9,132,230 B2 | 9/2015 | Blomquist | |
| 9,789,251 B2 | 10/2017 | Robert et al. | |
| 2004/0163977 A1 * | 8/2004 | Sedon | E05B 73/0023 |
| | | | 206/308.2 |
| 2007/0269324 A1 * | 11/2007 | Goldor | F04B 43/12 |
| | | | 417/474 |
| 2009/0221964 A1 * | 9/2009 | Rotem | A61M 5/16813 |
| | | | 604/151 |
| 2010/0145300 A1 | 6/2010 | Shelton et al. | |
| 2010/0156633 A1 * | 6/2010 | Buck, Jr. | A61B 5/7475 |
| | | | 340/540 |
| 2010/0160861 A1 * | 6/2010 | Causey, III | A61M 5/1456 |
| | | | 604/131 |
| 2011/0060284 A1 * | 3/2011 | Harr | A61M 5/14244 |
| | | | 604/153 |
| 2015/0285404 A1 * | 10/2015 | Koyama | A61M 39/281 |
| | | | 248/74.2 |
| 2017/0028126 A1 * | 2/2017 | Moosai | F16B 45/00 |

OTHER PUBLICATIONS

"Operator's Manual CADD-Prizm VIP Model 6100 and 6101 Ambulatory Infusion Pump", Smiths Medical MD, Inc., 2004.
"CADD-PLUS Ambulatory Infusion Pump Model 5400 Operator's Manual", SIMS Deltec, Inc. 2000.
"Operator's Manual CADD-Prizm VIP Model 6100 and 6101 Ambulatory Infusion Pump", SIMS Deltec, Inc., 2000.

* cited by examiner

LOW-COST AMBULATORY MEDICAL PUMP

CROSS-REFERENCE TO RELATED APPLICATION

This application is a continuation of U.S. application Ser. No. 14/471,102, filed Aug. 28, 2014, and hereby incorporated by reference.

BACKGROUND OF THE INVENTION

The present invention relates to compact infusion pumps for ambulatory use and in particular to an infusion pump design to reduce the costs of medical care delivery.

Medical pumps, such as infusion pumps, are known for computer-controlled delivery of medication (henceforth medicaments) to patients over a period of time. Recently, battery-powered compact infusion pumps have become available that permit the patient to remain active (ambulatory), for example, in a home environment away from a clinic or hospital during the treatment.

Typically the medicament is provided in a flexible bag that may be connected to an IV line which in turn attaches to a needle or port communicating with the patient. A nurse or other healthcare professional ministering to the patient receives the medicament, reviews the medicament description for correctness, and enters the desired dose and rate into the pump. The IV line is then installed in the portable pump and the assembly placed in a pack or other carrying apparatus that may be retained on the patient. The medicament may be delivered as the patient proceeds through normal life activities until the full dose is complete. The patient may then return the assembly to the nurse or health care professional who may provide a new bag of medicament and IV line, and may reprogram the pump for new treatment.

Pumps suitable for ambulatory use can have high total operating costs driven in part by the cost of the pump itself which must meet exacting medical standards while being compact, lightweight, and ruggedized for portable use. The present inventors have determined further that the recovery rate of ambulatory pumps is historically low. Failure to recover the pump can occur when pumps are used in end-of-life treatment, or are damaged or lost in the field.

High operating costs associated with ambulatory pumps necessarily limit the availability of the use of such medical devices to some individuals even though the pump could greatly improve the quality of care.

SUMMARY OF THE INVENTION

The present invention provides a cost-reduced ambulatory pump intended to increase availability and acceptability of ambulatory infusion. Lower cost is obtained by designing the pump with a component's short operating life specification, recognizing that the field operating life of such pumps is relatively short as biased by low pump recovery rates. Safety is ensured by incorporating absolute operating life limits into the pump that prevent the pump from being used in excess of its design life. In particular, maximum pump volume and maximum operating time may be monitored and used to block further use of the pump if that use would exceed safe operating limits. The pump also provides an improved IV line clamp system reducing the material costs of a significant mechanical component of the pump.

Specifically, the invention provides an ambulatory infusion pump having a housing that holds an IV line support structure receiving an IV line set and a fluid pump communicating with the IV support structure to pump fluid through an IV line. The housing also includes an electronic computer commuting with the fluid pump and with a user interface for receiving programming commands from a clinician. During operation, the electronic computer monitors operation of the fluid pump to store at least one cumulative pump operation value indicating a cumulative operation of the fluid pump from a time of manufacture. The computer determines whether an amount of operation of the fluid pump necessary to implement received treatment protocol instructions will exceed the software-enforced service life of the ambulatory fluid pump reduced by at least one cumulative pump operation value, and if so, prevents further operation of the fluid pump.

It is thus a feature of at least one object of the invention to provide look-ahead lockout of the programming of the pump, and when such programming is for a treatment protocol that would exceed the design pump operating life value, such design pump operating life is set to allow the safe use of durability components.

The computer may further provide an indication to an individual providing the fluid pump operation instructions through the user interface that the pump has rejected the received treatment protocol instructions.

It is thus a feature of at least one embodiment of the invention to clearly indicate the occurrence of the lockout, for example, so that it is not interpreted as the need for service, increasing pump-associated costs.

The software-enforced service life and at least one cumulative pump operation value cannot be reset using the user interface.

It is thus a feature of at least one embodiment of the invention to prevent unauthorized recycling of unsafe pumps or unsafe modification of the pump.

The indication may be a visual display

It is thus a feature of at least one embodiment of the invention to make use of a pre-existing user program element to provide an indication of pump lockout.

The software-enforced service life and at least one cumulative pump operation value may be stored in nonvolatile memory.

It is thus a feature of at least one embodiment of the invention to reduce the chance of inadvertent or intentional resetting of the service limits by removing power from the pump.

The software-enforced service life and at least one cumulative pump operation value are stored so that they cannot be altered without disassembly of the pump to access internal electronic components.

It is thus a feature of at least one embodiment of the invention to provide hardware barriers to reuse of the pump beyond its safe service life.

The software-enforced service life and at least one cumulative pump operation value may be in units of volume of fluid pumped by the fluid pump.

It is thus a feature of at least one embodiment of the invention to provide a measure of pump operation which reveals wear of the critical pump element.

The software-enforced service life may be less than 100 liters.

It is thus a feature of at least one embodiment of the invention to limit pump operation to permit the use of lower-cost pump elements subject to more rapid wear, for example, employing lower-cost motors, simpler bearings and less expensive material subject to wear.

Alternatively or in addition, the software-enforced service life and at least one cumulative pump operation value may be units of time of operation of the fluid pump.

It is thus a feature of at least one embodiment of the invention to provide a measurement of pump field life that reveals exposure of the pump to environmental contaminants and the aging of pump components regardless of wear.

The software-enforced service life may be less than 1000 hours.

It is thus a feature of at least one embodiment of the invention to limit pump operation to accommodate pump element contamination and material aging.

The software-enforced service life and at least one cumulative pump operation value may be a combination of volume of fluid pumped by the fluid pump and time of operation of the fluid pump, and the program may compare both a volume of fluid to be pumped by the fluid pump against a volume of fluid of the software-enforced service life and compare a time of operation of the fluid pump against a time of operation of the ambulatory fluid pump, each service life reduced by respective cumulative pump operation values. When the amount of operation of the fluid pump necessary to implement the treatment protocol exceeds either adjusted software-enforced service lives, operation of the fluid pump is prevented.

It is thus a feature of at least one embodiment of the invention to combine two measures of service life together to provide a more robust definition of the life of the pump.

The program may further operate to allow entry through the user interface of a maximum flow rate for delivering medicament.

It is thus a feature of at least one embodiment of the invention to permit other safeguards to be determined by the clinician programming the pump.

The user interface may consist solely of manually operated electronic switches for the purpose of receiving user input.

It is thus a feature of at least one embodiment of the invention to provide a cost-reduced control commensurate with the desired low-cost design of the pump.

The computer program may further execute to require entry of a password sequence through the user interface for accepting or changing treatment protocol instructions.

It is thus a feature of at least one embodiment of the invention to provide pump programming consistent with use in an unsupervised setting.

The password sequence may make use of manually operated switches labeled for other purposes.

It is thus a feature of at least one embodiment of the invention to provide for password-secured settings without the need for additional password input capabilities.

In some embodiments, the housing may provide a generally rectangular volume having a an upper active portion and a lower clamp portion attachable to the upper active portion to hold the IV line therebetween extending along a longitudinal axis, and the upper active portion and lower clamp portion may releasably attach to each other at multiple points along opposed longitudinal interfacing edges.

It is thus a feature of at least one embodiment of the invention to provide a more robust IV line clamping system by minimizing the unsupported span of the clamp portion.

The upper active portion and lower clamp portion may releasably attach along a front longitudinal edge by inter-engaging sliding hooks and tabs wherein a front face of the housing exposes a slide operator movable in a first direction to slide the hooks, and a safety stop movable against a spring in a second direction different from the first direction to a state allowing sliding of the hooks.

It is thus a feature of at least one embodiment of the invention to better prevent accidental disengagement of the clamp portion and IV line during ambulatory use.

These particular objects and advantages may apply to only some embodiments falling within the claims and thus do not define the scope of the invention.

DETAILED DESCRIPTION OF THE PREFERRED EMBODIMENT

Figure 1:
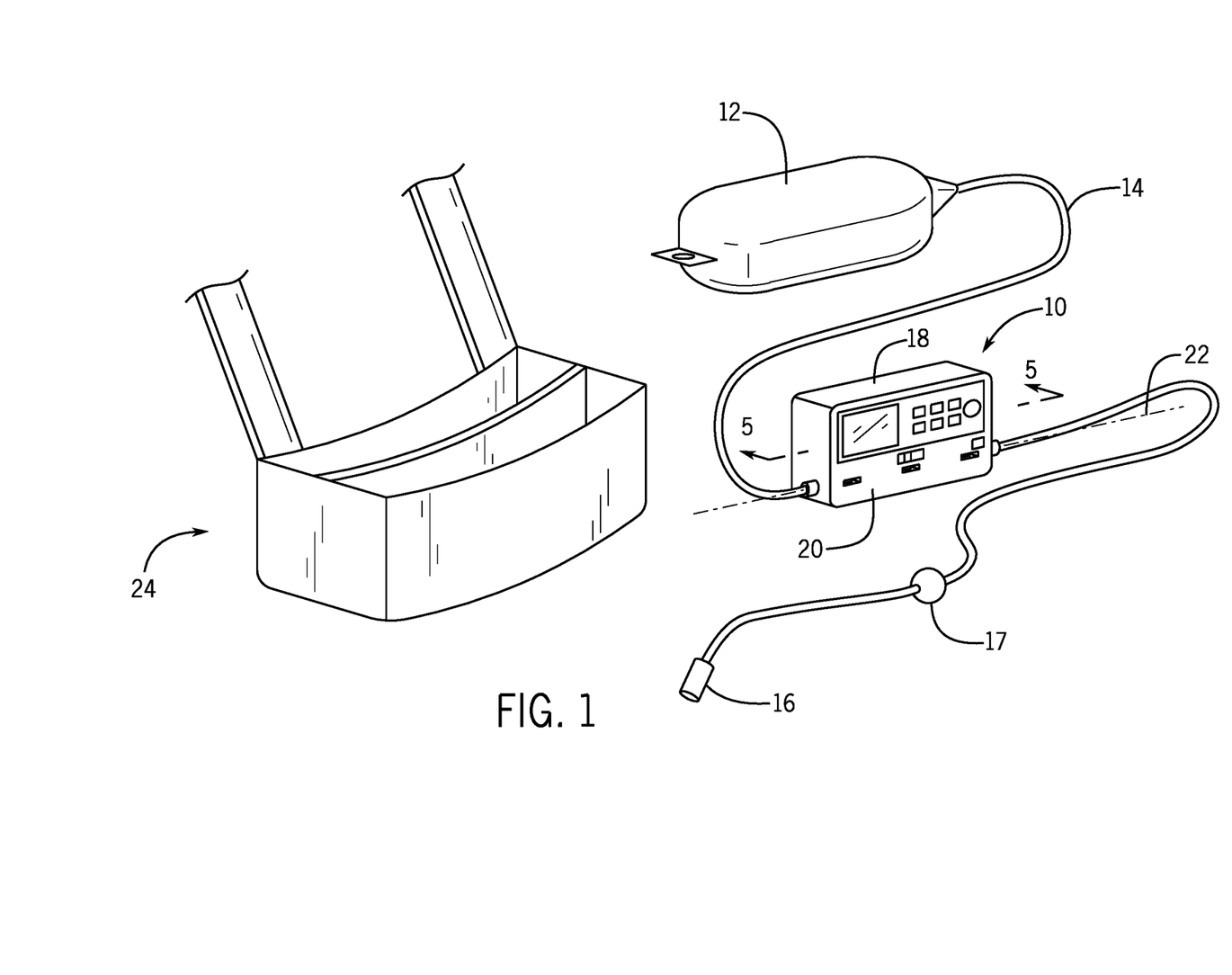
FIG. 1 is a simplified perspective view of the ambulatory pump assembly as provided to a patient.

Referring now to FIG. 1, an ambulatory pump 10 may operate in conjunction with a medicament bag 12 communicating with an IV line 14. The medicament bag 12 may be, for example, a flexible plastic bag of the type used to hold IV solutions, and the IV line 14 provides a flexible tube allowing the flow of medicament from the medicament bag 12 and a patient connector 16 that may communicate with the patient through a needle or port or the like. The IV line 14 may include a bubble filter 17 for removing included air bubbles, limiting the need for air bubble sensing.

The ambulatory pump 10 provides a two-part housing having an upper electronics portion 18 that may attach to a lower clamp portion 20 to receive the IV line 14 therebetween along a longitudinal axis 22 being generally the longest dimension of the housing of the ambulatory pump 10. As so received, the ambulatory pump 10 may pump liquid through the IV line 14 by peristaltic action.

In one embodiment, the ambulatory pump 10 is constructed to weigh less than a half pound and preferably less than 1.5"×2"×5" so as to be easily carried by the patient, for example, in a pouch 24 also sized to receive the medicament bag 12.

Figure 2:
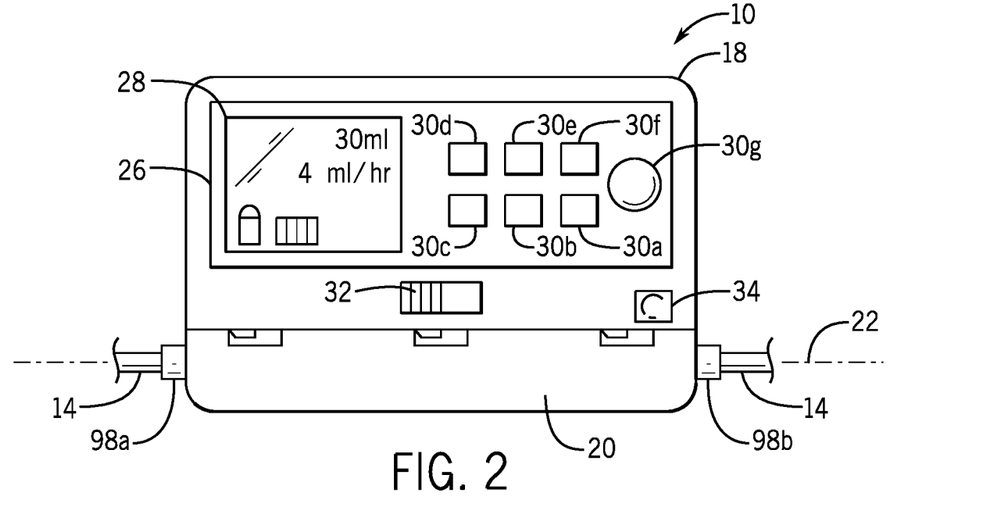
FIG. 2 is a front elevational view of the ambulatory pump showing inter-assembly of an upper active portion and lower clamp portion of the housing as separated by operation of dual release elements and showing a user interface comprising a display and manually operated buttons.

Referring now to FIG. 2, the housing of the upper active portion may present on its front surface a user interface 26 comprising, for example, a liquid crystal type display 28 for displaying symbols and alphanumeric characters under computer control. The user interface 26 also provides multiple membrane switch pushbuttons 30 that may be activated by a user. Generally, the pushbuttons include a limited number of controls including, in one embodiment, run and stop pushbuttons 30a and 30b, respectively, that will stop and start operation of the pump as will be described below; a rate pushbutton 30c allows setting of the maximum pumping rate of the ambulatory pump 10 in milliliters per hour by cycling through menu standard rates with each push (?). The pushbuttons also include a "volume to be infused" pushbutton 30d allowing user control of the maximum volume to be infused during a treatment protocol, also by cycling through standard settings with each push, as well as an information pushbutton 30 allowing the display of detailed information about the pump including remaining pump life (?). Pushbutton 30f allows the unit to be turned on and off to conserve power. A bolus pushbutton 30 allows short operation of the pump to deliver medicament in fixed patient controlled bolus quantities (?).

A lower edge of the upper electronics portion 18 provides for a clamp release slide 32 as will be described below and safety lock 34 that must be simultaneously activated to remove the lower clamp portion 20.

Figure 3:
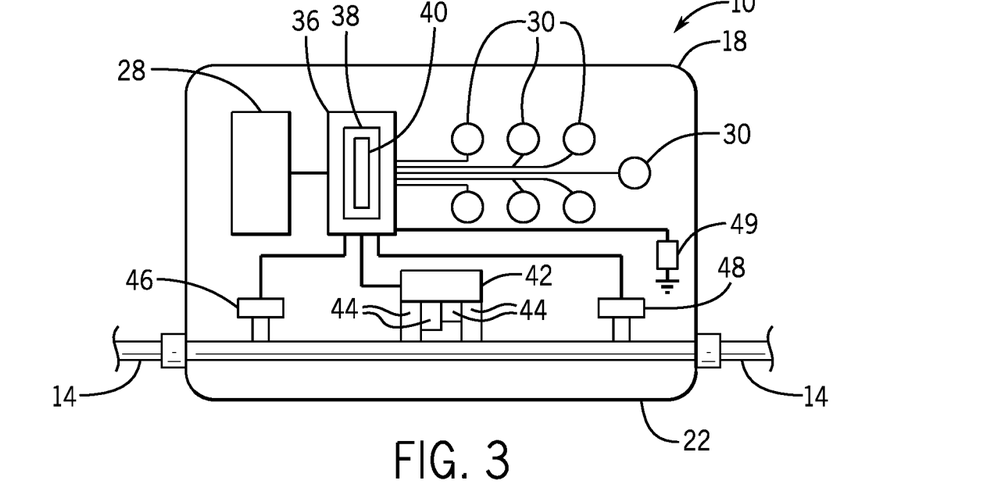
FIG. 3 is a simplified block diagram of the electronics of the pump of FIGS. 1 and 2 as controlled by internal electronic computer executing a stored program.

Referring now to FIG. 3, the ambulatory pump 10 may include a microcontroller 36 being an electronic computer having a self-contained nonvolatile memory 38 holding an operating program 40 and necessary storage variables as will be described below. The nonvolatile memory may comprise, for example, flash memory and/or read only memory, or other similar nonvolatile memory as context requires, which may store data values to be retained even in the absence of electrical power.

The microcontroller 36 also provides various inputs and output lines communicating, for example, with the display 28 for providing display information thereon and various pushbuttons 30 for receiving data related to their activation by user. In addition, the microcontroller 36 may provide control lines to the pump assembly 42 having, for example, an internal DC electric motor (not shown) operating through a gear system to activate peristaltic plunger elements 44 that may press against the contained IV line 14 to push fluid therethrough. As is understood in the art, generally the peristaltic plunger elements 44 extend in an undulating serpentine fashion to compress and release the tubing thereby moving fluid therethrough.

The microcontroller 36 may also communicate electrically with various sensors. For example, upstream and downstream pressure sensors 46 and 48 which can be used to ensure proper operation of the pump by detecting abnormal pressures. Generally each of the pressure sensors 46 and 48 may provide a spring-loaded plunger that presses into the outer wall of the IV line 14 to sense pressure. This throughwall measurement avoids the need for separate connections to the fluid-contacting pressure sensor and the problems of sterilization of a fluid-contacting pressure sensor. In such a through-tubing sensing system, the spring-loaded plunger deforms a portion of a wall of the IV line 14 as held against a backstop. Under a known spring biasing force, the amount of deflection of the wall may be measured to deduce internal pressure. Generally, lower pressures of the contained medicament will allow greater deflection of the wall of the IV line 14 and higher pressures of contained medicament will allow less deflection of the wall of the IV line 14. The system may be calibrated for a particular material of the IV line 14.

All electrical components in the upper electronics portion 18 maybe supplied with power by a contained storage battery 49 that may provide its power directly or through standard power processing circuits such as regulators and the like.

Figure 4:
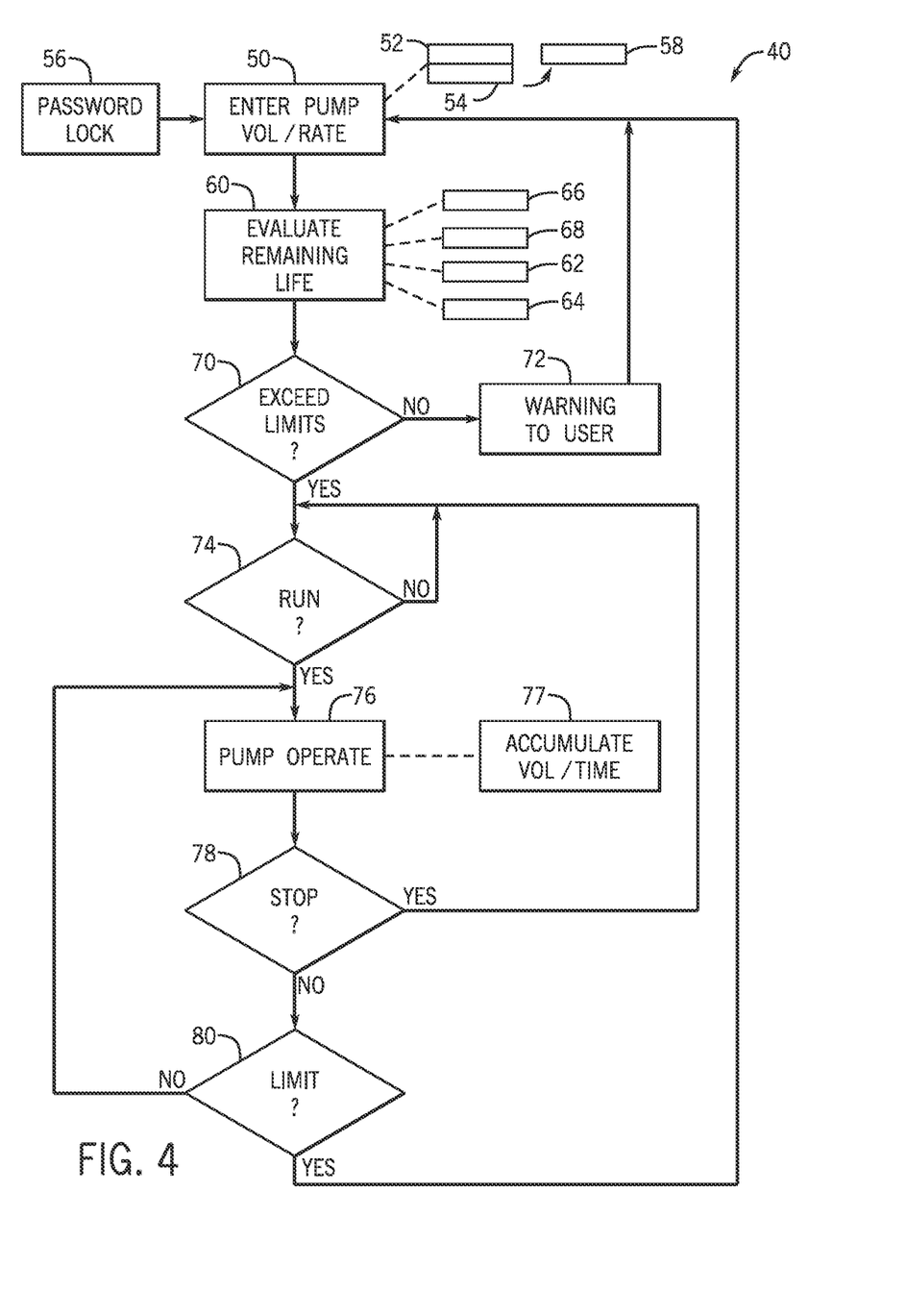
FIG. 4 is a flowchart of the stored program of FIG. 3 and the data structures used by that program.

Referring now to FIG. 4, during normal operation, a clinician will enter a total volume to be infused 52 and an infusion rate 54, as shown by process block 50, by using the user interface 26 shown in FIG. 2. In order to prevent tampering or inadvertent change in these values, their entry is accomplished through a password which must be entered first, indicated by process block 56. The password may employ a predetermined sequence of pressing the pushbuttons 30 (for example, after the unit is turned on but before it is programmed) such as pressing the run pushbutton 30a once and the stop pushbutton 30b twice. Such use of the pushbuttons 30 may be without regard to the actual labels of the button as, in this example, "run" and "stop".

The total volume to be infused 52 and the infusion rate 54 are then used to compute a total infusion time 58 that may, but need not be, a continuous time period but which may also be a cumulative time necessary for the infusion, contemplating that the infusion may be started and stopped by the patient. The total volume to be infused 52 and the infusion time 58 represent received protocol instructions (either direct or indirect) from a clinician describing the intended operating limits of the fluid pump in a treatment protocol.

At succeeding process block 60, the total volume to be infused 52 is compared against a preset software-enforced volume limit 62 of the pump 10 after the software-enforced volume limit 62 is reduced by the cumulative pumped volume 66. The cumulative pumped volume 66 is set to zero when the ambulatory pump 10 is manufactured and then increases with operation of the pump assembly 42. Similarly, the total infusion time 58 is compared against a preset software-enforced time limit 64 as reduced by the cumulative pump operation time 68. The cumulative pump operation time is also set to zero when the ambulatory pump 10 is manufactured and then increases with operation of the ambulatory pump 10 determined from activation of the on pushbutton 30f not necessarily including activation of the pump assembly 42. The net effect of process block 60 is to see if the intended treatment protocol can be performed before the service life of the pump has been exceeded.

If either the use-adjusted, software-enforced volume limit 62 or software-enforced time limit 64 have been exceeded, as determined at decision block 70, the program 40 proceeds to process block 72 and provides a warning that the treatment protocol may not be implemented as displayed on the display 28 of FIG. 2. The program 40 then returns the process block 50 without operation of the pump assembly 42 and a new password and new values must be entered if operation is to be continued. Decision block 70 may also check for adequate remaining battery energy for the protocol using an internal time-to-ampere-hour conversions based on the current drain of the ambulatory pump and comparing that against the estimated total ampere-hours of the battery.

If at decision block 70, the treatment protocol may be performed within the service limits of the pump 10, then the program proceeds to decision block 74 and may begin operation as indicated by process block 76, when the run pushbuttons 30a is pressed. The program loops until the run pushbutton 30a is pressed or the unit is switched off.

It will generally be understood that except through operation of the program 40 executing on the microcontroller 36, the values 66, 68, 62, and 64 contained in memory 38 may not be changed and the program 40 does not allow these values to be changed by the operator through the user interface 26. More generally, these values may not be changed by removing power from the ambulatory pump 10 (e.g. removing battery 49 shown in FIG. 3) and generally require disassembly of the pump 10 to obtain direct access to the pin structure of the microcontroller 36 and specialized equipment to access the memory directly if that is even possible. It is contemplated that these values may be stored in a way that cannot be changed without destruction of the ambulatory pump 10 or microcontroller 36.

The operation of the pump at process block 76 will normally monitor the pressure sensors 48 and 46 to ensure there is no upstream or downstream occlusion of medicament flow. Any such obstruction will cause a ceasing of the operation of the pump assembly 42 which may be reactivated after correction by the user. During process block 76, pump flow-rate is controlled by controlling the speed of the pump assembly 42 in open loop fashion according to the entered infusion rate 54. During operation, the pump's 76 accumulated time and pumping volume per process block 77 are used to update cumulative pumped volume 66 and cumulative pump operation time 68.

Periodically during operation of the pump at process block 76 (or enforced on an interrupt basis), decision block 78 may be polled to see if the stop pushbutton 30b has been pressed in which case the pump assembly 42 stops and the program 40 returns to decision block 74.

If the stop pushbutton 30b of decision block 78 has not been pressed, the program 40 proceeds to decision block 80 to determine whether the total volume through the ambulatory pump 10 during this treatment protocol has reached the total volume to be infused 52. If so, the program 40 loops back to process block 50, but if not the program returns to process block 76.

It should be noted that the updating of the cumulative values per process block 77 looks at actual rather than estimated hours and volumes pumped in contrast to the calculation of process block 60.

Figure 6:
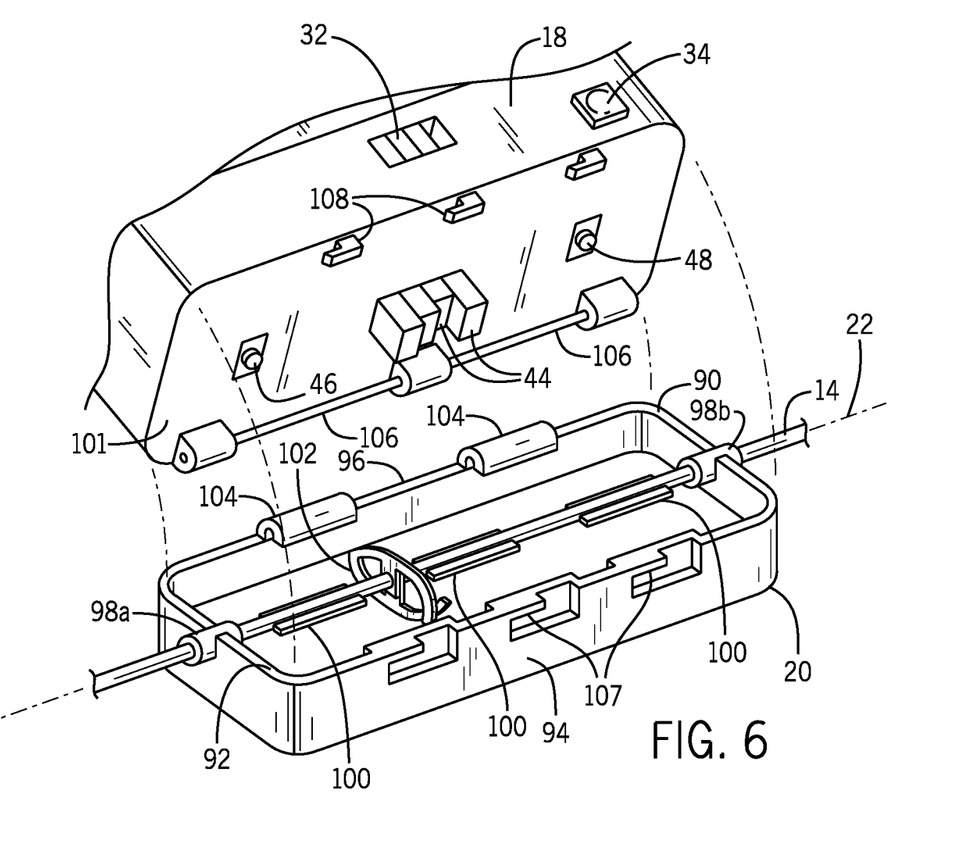
FIG. 6 is a perspective fragmentary view of the upper active portion and lower clamp portion as released showing various elements thereof.

Referring now to FIGS. 2 and 6, the upper surface of the lower clamp portion 20 may provide for a shallow tray having upstanding peripheral longitudinally-opposed end walls 90 and 92, these walls separating the opposed upstanding peripheral longitudinally-extending sidewalls 94 and 96. The end walls 90 and 92 may include notches receiving retention bushings 98a and 98b formed in the IV line 14 to prevent longitudinal movement of the IV line 14 with respect to the lower clamp portion 20 along the longitudinal axis 22.

Between the bushings 98a and 98b, the material of the IV line 14 may be replaced with a silicone material that is softer and more conducive to peristaltic pumping and through-wall pressure sensing. The portion of the IV line 14 within the tray of the lower clamp portion 20 may be held by guides 100 which form notches to align and retain the IV line 14 with the peristaltic plunger elements 44 and the downwardly extending operators of the pressure sensors 46 and 48 held in the bottom wall 101 of upper electronics portion 18. The guides 100 may also provide for backstops holding the IV line 14 against the pressure of the downwardly extending operators of the pressure sensors 46 and 48 and the peristaltic plunger elements 44.

The IV line 14 may pass through a spring bias clamp element 102 that automatically clamps the IV line 14 when the lower clamp portion 20 is separated from the upper electronics portion 18.

Rear sidewall 96 includes upwardly extending open hinge collars 104 spaced along its edge that may attached to and hinge about hinge pin 106 supported at a rear edge of the bottom wall 101 of the upper electronics portion 18, spaced below the bottom wall 101 and generally parallel to the longitudinal axis 22.

Front sidewall 94 includes longitudinally-extending tabs 107 that may be engaged by corresponding hooks 108 extending down from the front edge of the bottom wall 101 of the upper electronics portion 18 and activated by release slide 32 as will be described to move generally along the longitudinal axis 22. When the lower clamp portion 20 is attached by the interconnection of open hinge collars 104 and hinge pin 106 and pivoted upward toward the bottom 101, the hooks 108 may pass over and attach to the tabs 107 to retain the upper electronics portion 18 and lower clamp portion 20 together with the IV line 14 in proper alignment and clamp therebetween.

By attaching the lower clamp portion 20 to the upper electronics portion 18 at multiple points across the narrower dimension of the lower clamp portion 20, reduced flexure of the lower clamp portion 20 may be obtained (as opposed to attachment at end walls 92 and 90) against the forces of the peristaltic plunger elements 44 and pressure sensors 46 and 48 providing better alignment against minor tolerances and reduced flexure caused by the reduced unsupported span of the polymer material of the lower clamp portion 20. This allows reduced material costs for the lower clamp portion 20 and provides increased accuracy, for example, in the pressure sensing.

Figure 5:
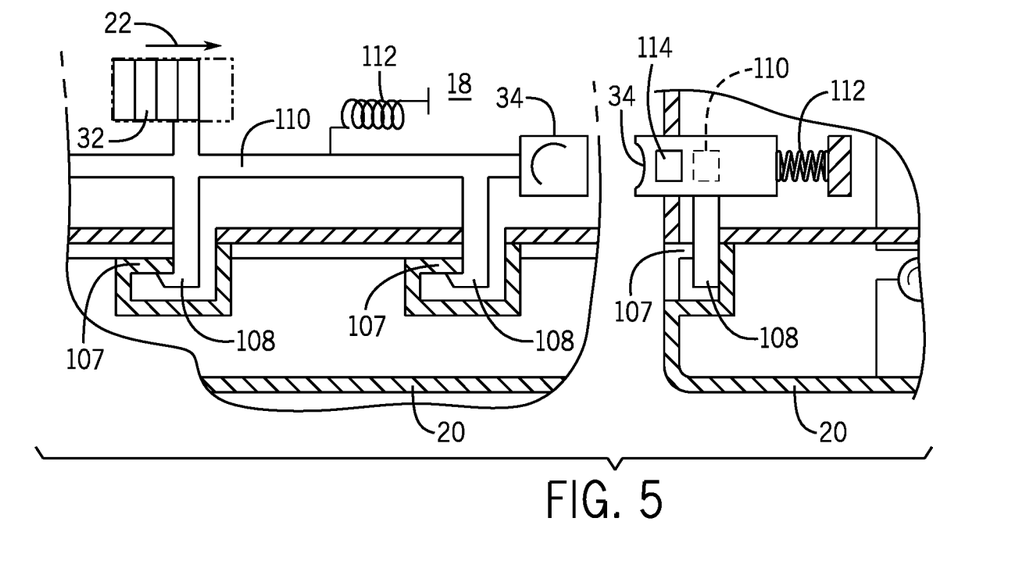
FIG. 5 is a first fragmentary cross-sectional view taken along 5-5 of FIG. 1 and a second perpendicular cross-section aligned therewith showing operation of the dual release elements of FIG. 2.

Referring now to FIG. 5, the downwardly extending hooks 108 may be attached to a common driver bar 110 that is longitudinally spring biased by a spring 112 into engagement with the tabs 107 tending to hold the lower clamp portion 20 against the upper electronics portion 18. The bar 110 may communicate with release slide 32 which may be pressed rightward against the biasing spring 112 to allow release of the hooks 108 from the tabs 107. Leftward motion of the bar 110 is only possible, however, when safety lock 34 is pressed inward against biasing spring 112 in a direction perpendicular to the longitudinal axis 22 allowing a longitudinally-extending opening 114 in the safety lock 34 to align with the driver bar 110 permitting rightward movement of an extension of the common driver bar 110 through the longitudinally-extending opening 114. Because the motion of the clamp release slide 32 and safety lock 34 are in different directions and they are located in separated positions, accidental release of the lower clamp portion 20 is greatly reduced.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context. Indication is used herein to mean any type of sense to indication including an audio alarm, visual display or other computer-controlled activation (motor buzz, etc.)

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

References to "a microprocessor" and "a processor" or "the microprocessor" and "the processor," can be understood to include one or more microprocessors or other types of computers, gate arrays or the like that can execute programs and communicate with each other. Furthermore, references to memory, unless otherwise specified, can include one or more processor-readable and accessible memory elements and/or components that can be internal to the processor-controlled device, external to the processor-controlled device, and can be accessed via a wired or wireless network. The term manual pushbuttons means buttons that may be operated by finger touch or the like including touchscreen and passive switch and mechanical switch.

It will be appreciated that the look-ahead operation of the ambulatory pump 10 described herein is consistent both with anticipatory locking of the pump so that the pump does not exceed the service values, as well as setting the service values to a value below the actual longest desired service value by amount of the typical treatment protocol and allowing the treatment protocol to exceed the service value once, and then locking out pump. In this latter case, the pump lockout anticipates that the next treatment protocol would exceed the remaining operating time or volume (which is a negative value) and need not actually accept a new protocol.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications, are hereby incorporated herein by reference in their entireties.

We claim:

1. A medical tube assembly detachable from a pump housing holding outwardly extending peristaltic actuator elements, comprising:
    a flexible medical tube adapted to communicate between an external fluid bag and a patient connection; and
    a substantially rigid frame having first and second opposed longitudinal walls extending along a longitudinal axis of the frame defined by a longest dimension of the frame and separated by first and second opposed end walls and retaining the medical tube against movement therein wherein the medical tube extends along the longitudinal axis of the frame, the frame including a connector detachably attaching the frame to the pump housing and medical tube guides to align the medical tube along the longitudinal axis of the frame and with the peristaltic actuator elements to permit peristaltic pumping of liquid of the medical tube when the frame is attached to the pump housing;
    wherein the connector provides a first attachment element including a first hinge portion extending and positioned along one of the first and second opposed longitudinal walls of the frame and to releasably attach to a second hinge portion of the pump housing wherein the first hinge portion is attachable to the second hinge portion to thereby pivot about a hinge axis extended along the longitudinal axis of the frame;
    wherein the connector provides a second attachment element including receiving tabs extending along the other of the first and second opposed longitudinal walls of the frame and to releasably receive corresponding hooks of the pump housing by movement of the corresponding hooks generally along the pump housing and the other of the first and second longitudinal walls of the frame;
    wherein the medical tube is comprised of a first material positioned outside of the frame and a second material softer than the first material, the softer material positioned between the opposed first and second ends of the frame.

2. The medical tube assembly of claim 1 wherein one of the first and second hinge portions includes first and second hinges spaced longitudinally along the one of the first and second opposed longitudinal walls of the frame and a longitudinal wall of the pump housing and is receivable by including a pin of the other of the first and second hinge portions extending longitudinally along the other of the frame and the pump housing.

3. The medical tube assembly of claim 2 wherein the first and second hinges are open collars with a first longitudinal edge attached to the one of the first and second opposed longitudinal wall of the frame and a second longitudinal edge extending away from the pump housing.

4. The medical tube assembly of claim 1 wherein the corresponding hooks and the receiving tabs includes three hooks and three receiving tabs.

5. The medical tube assembly of claim 1 wherein the second attachment element further comprises an actuator wherein the corresponding hooks move generally along the pump housing and the other of the first and second longitudinal walls of the frame when the actuator is moved along the longitudinal axis.

6. The medical tube assembly of claim 5 wherein movement of the corresponding hooks along the longitudinal axis is permitted only when activated by a push button pressable in a direction perpendicular to the longitudinal axis.

7. The medical tube assembly of claim 5 wherein the actuator is moved along a sidewall of one of the frame and the pump housing.

8. The medical tube assembly of claim 1 wherein the corresponding hooks and the receiving tabs are spring biased into engagement with the receiving tabs tending to hold the frame against the pump housing.

9. The medical tube assembly of claim 8 wherein the corresponding hooks are beveled to move the corresponding hooks against the spring biasing with attachment but not with detachment.

10. The medical tube assembly of claim 1 wherein the pump housing further holds pressure sensors and the medical tube guides further align the medical tube retained by the frame with the pressure sensors to detect a fluid pressure through the medical tube.

11. The medical tube assembly of claim 1 wherein the second material is silicone.

12. The medical tube assembly of claim 1 wherein the frame further holds a spring biased pinch element configured to compress the medical tube to prevent fluid flow therethrough when the frame and the pump housing are separated.

13. The medical tube assembly of claim 1 wherein the frame is releasably attachable to the pump housing to form a continuous outer surface with an exterior of the pump housing.

14. The medical tube assembly of claim 1 wherein the first and second opposed end walls of the frame provide opposed first and second notches, respectively, the first notch receiving a first fixed bushing of the medical tube and the second notch receiving a second fixed bushing of the medical tube.

15. An ambulatory pump comprising the medical tube assembly of claim 1 and further comprising the pump housing, the pump housing further holding:
- a pump communicating with the medical tube assembly to pump fluid through the medical tube by peristaltic compression of the medical tube;
- a user interface for receiving programming commands from a clinician; and
- an electronic computer communicating with the pump and the user interface and executing a program stored in a non-transitory computer readable storage medium to control operation of the pump.

16. The ambulatory pump of claim 15 wherein the medical tube assembly has a total weight less than one pound and has dimensions of less than 1.5" by 2" by 5".

17. The ambulatory pump of claim 15 wherein the electronic computer communicates with the pump and the user interface to execute the program stored in the non-transitory computer readable storage medium to:
  (i) monitor operation of the pump to store at least one cumulative pump operation value indicating a cumulative operation of the pump from a time of manufacture of the pump;
  (ii) receive treatment protocol instructions through the user interface describing an intended future operating limit of the pump to pump fluid through the medical tube in a treatment protocol;
  (iii) determine whether an amount of operation of the pump necessary to implement received treatment protocol instructions will exceed a predetermined software-enforced service life of the pump reduced by the at least one cumulative pump operation value; and
  (iv) when the amount of operation of the pump necessary to implement the treatment protocol exceeds the software-enforced service life of the pump reduced by the at least one cumulative pump operation value, prevent operation of the pump.

18. A medical tube assembly detachable from a pump housing holding outwardly extending peristaltic actuator elements, comprising:
- a flexible medical tube adapted to communicate between an external fluid bag and a patient connection; and
- a substantially rigid frame having first and second opposed longitudinal walls extending along a longitudinal axis of the frame defined by a longest dimension of the frame and separated by first and second opposed end walls and retaining the medical tube against movement therein wherein the medical tube extends along the longitudinal axis of the frame, the frame including a connector detachably attaching the frame to the pump housing and medical tube guides to align the medical tube along the longitudinal axis of the frame and with the peristaltic actuator elements to permit peristaltic pumping of liquid of the medical tube when the frame is attached to the pump housing;
- wherein the connector provides a first attachment element including a first hinge portion extending and positioned along one of the first and second opposed longitudinal walls of the frame and to releasably attach to a second hinge portion of the pump housing, wherein the first hinge portion is attachable to the second hinge portion to thereby pivot about a hinge axis extended along the longitudinal axis of the frame, and wherein one of the first and second hinge portions includes first and second hinges spaced longitudinally along the one of the first and second opposed longitudinal walls of the frame and a longitudinal wall of the pump housing and is receivable by a pin of the other of the first and second hinge portions extending longitudinally along the other of the frame and the pump housing;
- wherein the connector provides a second attachment element including receiving tabs extending along the other of the first and second opposed longitudinal walls of the frame and to releasably receive corresponding hooks of the pump housing;
- wherein the medical tube is comprised of a first material positioned outside of the frame and a second material softer than the first material, the softer material positioned between the opposed first and second ends of the frame.

* * * * *